United States Patent
Sugiyama et al.

(10) Patent No.: US 7,300,632 B2
(45) Date of Patent: Nov. 27, 2007

(54) SWAB TESTING DEVICE AND METHOD

(76) Inventors: Nobuyuki Sugiyama, 3-29-11, Takadanobaba, Shinjuku-Ku, Tokyo (JP); Katsumi Horiuchi, 1-12-5, Yutaka-Cho, Shinagawa-Ku, Tokyo (JP)

( * ) Notice: Subject to any disclaimer, the term of this patent is extended or adjusted under 35 U.S.C. 154(b) by 622 days.

(21) Appl. No.: 10/390,050

(22) Filed: Mar. 17, 2003

(65) Prior Publication Data

US 2004/0014237 A1    Jan. 22, 2004

(30) Foreign Application Priority Data

Mar. 18, 2002 (JP) .............................. 2002-074645
Apr. 11, 2002 (JP) .............................. 2002-108804

(51) Int. Cl.
*G01N 30/00* (2006.01)

(52) U.S. Cl. .................... 422/102; 422/50; 422/55; 422/56; 422/57; 422/58; 422/68.1; 422/99; 422/100; 422/104

(58) Field of Classification Search ............ 422/50, 422/55, 56, 57, 58, 68.1, 99, 100, 102, 104
See application file for complete search history.

(56) References Cited

U.S. PATENT DOCUMENTS

| | | | |
|---|---|---|---|
| 3,918,435 A | | 11/1975 | Beall |
| 5,078,968 A | | 1/1992 | Nason |
| 5,543,115 A | * | 8/1996 | Karakawa .................... 422/102 |
| 5,827,675 A | * | 10/1998 | Skiffington et al. ............ 435/8 |
| 6,059,474 A | | 5/2000 | Huang |
| 2001/0008614 A1 | * | 7/2001 | Aronowitz .................. 422/101 |

FOREIGN PATENT DOCUMENTS

| | | |
|---|---|---|
| EP | 699 591 A2 | 6/1996 |
| JP | 03 000661 U | 1/1991 |

* cited by examiner

*Primary Examiner*—Jill Warden
*Assistant Examiner*—Samuel P. Siefke
(74) *Attorney, Agent, or Firm*—Marshall & Melhorn, LLC (57) ABSTRACT

A swab testing device comprises a container (1) containing a diluent (7), a cap (10, 20) detachably mounted on an opening of the container, an elongating stick (4) secured to or integral with the cap, and a cotton swab (5) connected to a leading end of the stick and immersed in the diluent when the container opening is closed with the cap. The cap provides a communicating channel (12, 14, 27, 31) communicatable with the interior (6) of the container and also communicatable with the atmosphere by an aperture (23a) formed on the cap. The cap also includes a lid (15, 25) by which the aperture may be opened and closed. Any liquid in the container may be discharged through the communicating channel and the aperture, when the lid is opened to communicate the channel with the atmosphere through the aperture, even when the container opening remains closed with the cap.

9 Claims, 6 Drawing Sheets

SWAB TESTING DEVICE AND METHOD

BACKGROUND OF THE INVENTION

1. Field of the Invention

The present invention relates to a swab testing device that is suitable for use in experimenting a swab test to inspect sanitary condition of apparatus, materials, equipments, instruments, cookware and any other items to be used in food manufacturing and processing plants and restaurants' kitchens, to thereby prevent any bacteriological contaminant to be incorporated into foods. Such a device may also be used to inspect sanitary condition of worker fingers. The present invention also relates to a novel swab testing method by using such a device.

2. Description of the Prior Art

Sanitary condition of apparatus, materials, equipments, instruments, cookware and any other items to be used in food manufacturing and processing plants and restaurants' kitchens must be inspected to examine and prove bacteriological or microbiological safety of foods. Since workers' hands and fingers may also be bacteriologically or microbiologically contaminated, even after being washed, sanitary condition of workers' hands and fingers should also be inspected. Such inspection is in general experimented to inspect the number of microbe, particularly colon bacilli in foods. In some case, further inspection is experimented to inspect the number of *staphylococcus aureus* and yeast funges. Mold test may optionally be carried out.

Swab test has been widely used as one of typical inspection measures. Swab test is usually carried out by the steps of preparing a cotton swab or gauze sterilized in 1 ml of 0.1% peptone incorporated saline, swabbing down a surface of an item to be inspected with the sterilized cotton swab or gauze, containing the cotton swab or gauze into a container bottle together with 9 ml of 0.1% peptone incorporated saline, and shaking the bottle to stir the mixture to prepare a test sample. This manner of the swab test method, however, is troublesome and could not provide reliable results when carried out in most of small-scaled plants and restaurant's kitchen having no well-equipped laboratory.

The swab test has also been carried out clinically to swab down an affected part on nose, ear or throat with a sterilized cotton swab or gauze to collect a sample. The conventional clinical swab test method comprises the steps of collecting a sample with a sterilized cotton swab or gauze, immersing the cotton swab or gauze with phosphoric buffer in a test tube, and urging the cotton swab or gauze to contact under pressure with the inner wall of the test tube, during ascend of the cotton swab or gauze, thereby squeezing the sample out of the cotton swab or gauze into the buffer. This manner of the clinical swab test method is also troublesome and skill-requiring operation.

A swab testing kit or device, disclosed in Japanese utility model registration No. 3,000,661 comprises a container containing a diluent and provided with a section having a decreased inside diameter, a cap detachably mounted on an opening of the container, a stick secured to or integral with the cap, and a cotton swab attached to a leading end of the stick and immersed in the diluent when the cap is mounted on the container opening. During drawing-up operation of the cap after being detached from the container, the diluent or sample liquid impregnated with the cotton swab is squeezed to be removed therefrom and collected again into the diluent when the cotton swab passes through the decreased inside diameter section of the container. More specifically, when the container is first uncapped, an excessive amount of the diluent contained in the cotton swab is removed therefrom, so that the cotton swab suitably wetted with the diluent may be used for swab test operation. After completing the swab test, the cotton swab containing the sample liquid is inserted into the container through the opening that is then closed with the cap. During such capping operation, an appropriate amount of the sample liquid contained in the cotton swab is removed therefrom to drop down into the diluent in the container.

This swab testing kit or device has been found to be very useful, because a swab test may be achieved by simple operation, even by unskilled person and even at small-scaled plants and restaurant's kitchen with no laboratory.

With the above-described prior art swab test kit or device, it becomes very easy to carry out the swab test and collect a sample liquid that can expect a reliable test results. However, even with this kit or device, it is necessary that the sample liquid in the container, after being uncapped, is pipetted into a culture medium in a laboratory dish or tube. Otherwise, the uncapped container is tilted to discharge some amount of the sample liquid out of the container into the culture medium. In any way, it is very difficult to pipette a required amount of the sample liquid. The former operation requires a pipette longer enough than a distance from the opening of the container to the level of the sample liquid. The latter operation requires tilting of the uncapped container with scrupulous attention, otherwise a greater amount of the sample liquid is discharged from the container to overflow the laboratory dish or tube.

SUMMARY OF THE INVENTION

Accordingly, it is an object of the present invention to overcome the drawbacks and disadvantages of the prior art swab test kit or device and, more specifically, to provide a novel swab testing device that is particularly easy to pipette a required amount of a sample liquid in a container to a culture medium in a laboratory dish or tube.

Another object of the present invention is to provide a novel swab testing method, which may easily be done even by unskilled person and even at private food plants with no laboratory.

To achieve these and other objects, in accordance with an aspect of the present invention, there is provided a swab testing device having a container containing a diluent, a cap detachably mounted on an opening of the container, an elongating stick secured to or integral with the cap, and a cotton swab connected to a leading end of the stick and immersed in the diluent when the container opening is closed with the cap, characterized in that:

(a) the cap provides a communicating channel communicatable with the interior of the container and also communicatable with the atmosphere by an aperture formed on the cap;

(b) the cap also includes a lid by which the aperture may be opened and closed; and (c) any liquid in the container may be discharged through the communicating channel and the aperture, thereof, when the lid is opened to communicate the channel with the atmosphere through the aperture, even when the container opening remains closed with the cap.

In a preferred embodiment of the present invention, the underside of the cap includes a downward hollow tube with a plurality of slits extending therethrough, and the hollow tube and the slits constitute the communicating channel. The slits may be equally spaced, radially extending slits.

In another preferred embodiment of the present invention, the underside of the cap includes a downward hollow tube having an inside diameter slightly greater than an outside diameter of the stick, and the hollow tube is provided with a plurality of inward projections cooperating with each other to surround and support the stick. The upper ends of at least one of the inward projections inwardly extend toward a gap between the bottom of the hollow tube and the top of the stick. In this embodiment, the spaces between adjacent inward projections and between the hollow tube and the stick and the gap between the bottom of the hollow tube and the top of the stick will constitute the communicating channel. The inward projections may be integrally formed on the inside of the hollow tube with equal spacing.

In still another preferred embodiment of the present invention, the container is provided with a reference below a level of a liquid contained therein and plurality of scales still below the reference, when the container is held with the cap down. The reference indicates a liquid level from which pipetting should start. Each scale indicates an amount of the liquid that has been discharged or pipetted.

In still another preferred embodiment of the present invention, the container includes squeezing means for removing and recovering an excessive amount of the liquid contained in the cotton swab when the cotton swab is drawn from the container during uncapping operation, as well as for removing and recovering the sample liquid contained in the cotton swab when the cotton swab is inserted into the container during capping operation after the cotton swab has been used to swab down a surface of the subject of swab test.

The stick of the swab testing device according to the present invention may be hollow, in which case a hollow interior of the stick may also be a part of the communicating channel. The stick of the swab testing device according to the present invention may also be telescopic.

In accordance with another aspect of the present invention, there is provided a swab testing method comprising the steps of:

(i) preparing a swab testing device having a container containing a diluent, a cap detachably mounted on an opening of the container and providing a communicating channel communicatable with the interior of the container and also communicatable with the atmosphere by an aperture formed on the cap, a lid connected to the cap for opening and closing the aperture, an elongating stick secured to or integral with the cap, and a cotton swab attached to a leading end of the stick and immersed in the diluent when the container opening is closed with the cap;

(ii) removing the cap from the container;

(iii) using the cotton swab impregnated with the diluent to swab down a surface of the subject to be bacteriologically or microbiologically inspected;

(iv) inserting the cotton swab with a sample into the container and close the container with the cap; and (v) opening the lid and holding the swab testing device substantially upside-down, with the container being still closed with the cap, to allow a predetermined amount of liquid in the container to be discharged through the communicating channel and the aperture of the cap and thereby pipetted into any container for laboratorial sanitary inspection.

In accordance with still another aspect of the present invention, there is provided a swab testing method comprising the steps of:

(i) preparing a swab testing device having a container containing a diluent and provided with a reference below a level of a liquid contained therein and plurality of scales still below the reference, when the container is held with the cap down, a cap detachably mounted on an opening of the container and providing a communicating channel communicatable with the interior of the container and also communicatable with the atmosphere by an aperture formed on the cap, a lid connected to the cap for opening and closing the aperture, an elongating stick secured to or integral with the cap, and a cotton swab attached to a leading end of the stick and immersed in the diluent when the container opening is closed with the cap;

(ii) removing the cap from the container;

(iii) using the cotton swab impregnated with the diluent to swab down a surface of the subject to be bacteriologically or microbiologically inspected;

(iv) inserting the cotton swab with a sample into the container and close the container with the cap;

(v) opening the lid and holding the swab testing device substantially upside-down, with the container being still closed with the cap, (v-1) to allow some amount of liquid in the container to be discharged through the communicating channel and the aperture of the cap, until the liquid level reaches the reference of the container; and (v-2) to allow a predetermined amount of liquid in the container to be discharged through the communicating channel and the aperture of the cap and thereby pipetted into any container for laboratorial sanitary inspection, by reference to a selected one of the scales of the container.

In accordance with still another aspect of the present invention, there is provided a swab testing method comprising the steps of:

(i) preparing a swab testing device having a container containing a diluent, a cap detachably mounted on an opening of the container and providing a communicating channel communicatable with the interior of the container and also communicatable with the atmosphere by an aperture formed on the cap, a lid connected to the cap for opening and closing the aperture, an elongating stick secured to or integral with the cap, a cotton swab attached to a leading end of the stick and immersed in the diluent when the container opening is closed with the cap and squeezing means for removing and recovering an excessive amount of a liquid contained in the cotton swab when the cotton swab is drawn from the container during uncapping operation, as well as for removing and recovering a liquid contained in the cotton swab when the cotton swab is inserted into the container during capping operation after the cotton swab has been used to swab down a surface of the subject to be bacteriologically or microbiologically inspected;

(ii) removing the cap from the container, during which the cotton swab is treated with the squeezing means so that an excessive amount of liquid contained in the cotton swab is removed therefrom and recovered back into the container;

(iii) using the cotton swab impregnated with a suitable amount of the diluent to swab down the surface of the subject;

(iv) inserting the cotton swab with a sample into the container and close the container with the cap, during which the cotton swab is again treated with the squeezing means so that some amount of the sample attached to the cotton swab as a result of swab test is removed therefrom to be collected into the container;

(v) opening the lid and holding the swab testing device substantially upside-down, with the container being still closed with the cap, (v-1) to allow some amount of liquid in the container to be discharged through the communicating channel and the aperture of the cap, until the liquid level reaches the reference of the container; and (v-2) to allow a predetermined amount of liquid in the container to be discharged through the communicating channel and the aperture of the cap and thereby pipetted into any container for laboratorial sanitary inspection, by reference to a selected one of the scales of the container.

BRIEF DESCRIPTION OF THE DRAWINGS

Other objects and advantages of the present invention can be understood from the following description when read in conjunction with the accompanying drawings in which.

DETAILED DESCRIPTION OF THE PREFERRED EMBODIMENT

Figure 1:
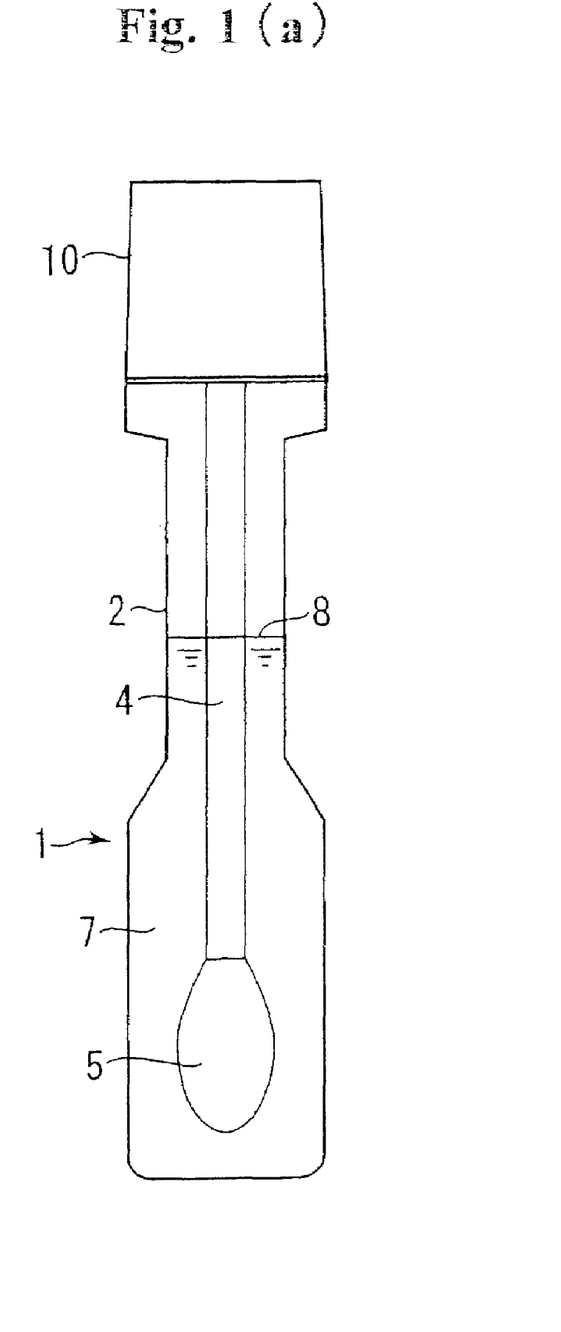
FIG. 1(a) and FIG. 1(b) are front and side views of a swab testing device according to an embodiment of the present invention.

In specific reference to FIGS. 1(a) and 1(b), a preferred embodiment of a swab testing device has a container 1 made from soft, flexible material that is deformable under compression, including high density polyethylene (HDPE). A top opening of container 1 may be hermetically closed by a detachable cap 10 having an integral, elongated stick 4 with a cotton swab 5 at a leading end thereof. When container 1 is capped, stick 4 is completely received in container 1 in coaxial relation with each other, and cotton swab 5 is positioned in vicinity to the bottom of container 1, as best shown in FIG. 1(a).

Cap 10 may be designed to provide any suitable means to achieve detachable mounting onto the top opening of container 1, as far as it provides a hermetical closure to the top opening of container 1. For example, cap 10 has an internal thread that can be screwed into an external thread around the top opening of container 1. In another embodiment, cap 10 is press-fit onto the container mouth.

Stick 4, that may be solid or hollow, is made from suitable plastic material such as polypropylene (PP) and fitted to a center of the underside of cap 10 by screw, bonding or any other suitable means that provides practically inseparable connection between stick 4 and cap 10. In the illustrated embodiment, as specifically shown in FIG. 2, a hollow tube 11 is formed integrally with cap 10, which extends downward from a center of the underside of cap 10 to engagingly receive the upper end of stick 4. In another embodiment, stick 4 is an integral part of cap 10, in which case stick 4 is formed integrally with cap from the same plastic material.

A predetermined amount of diluent 7 is in advance received in container 1. An example of diluent 7 is 10 ml of saline to which 0.1% of peptone is incorporated. As described above, when cap 10 is sealingly fitted onto the mouth of container 1, cotton swab 5 secured to the lower end of stick 4 is positioned in vicinity to the bottom of container 1 so that it is completely immersed within diluent 7 in container 1, as best seen in FIG. 1(a). In other words, the position of cotton swab 5 in the capped container 1 is always lower than a liquid level 8 of diluent 7.

Container 1 is substantially cylindrical, comprising an upper portion including the neck surrounding the top opening, a lower portion that is filled with dilution 7 and an intermediate portion having a diameter considerably smaller than those of upper and lower portions. The reduced intermediate portion 2 has a pair of opposed, substantially flat surfaces 2, 2 with a distance therebetween being slightly greater than the diameter of cotton swab 5.

A series of scales 3 are represented on one surface 2 of the intermediate container portion. As shown in FIG. 1(b), scales 3 are shown in reverse orders so that the liquid level 8 of any liquid in container 1 can easily and accurately recognized in reference to scales 3 when the capped container 1 is held upside down. As will be described in more detail, scales 3 are used to measure the amount of liquid to be pipetted from container 1 to a laboratory dish or tube to be subjected to a swab test or laboratorial sanitary inspection. Among scales identified by figures "0" to "6" shown on surface 2 in this embodiment, a scale identified by figure "0" indicates a reference level and other scales identified by figures "1" to "6" indicates the liquid amount discharged from container 1.

Figure 2:
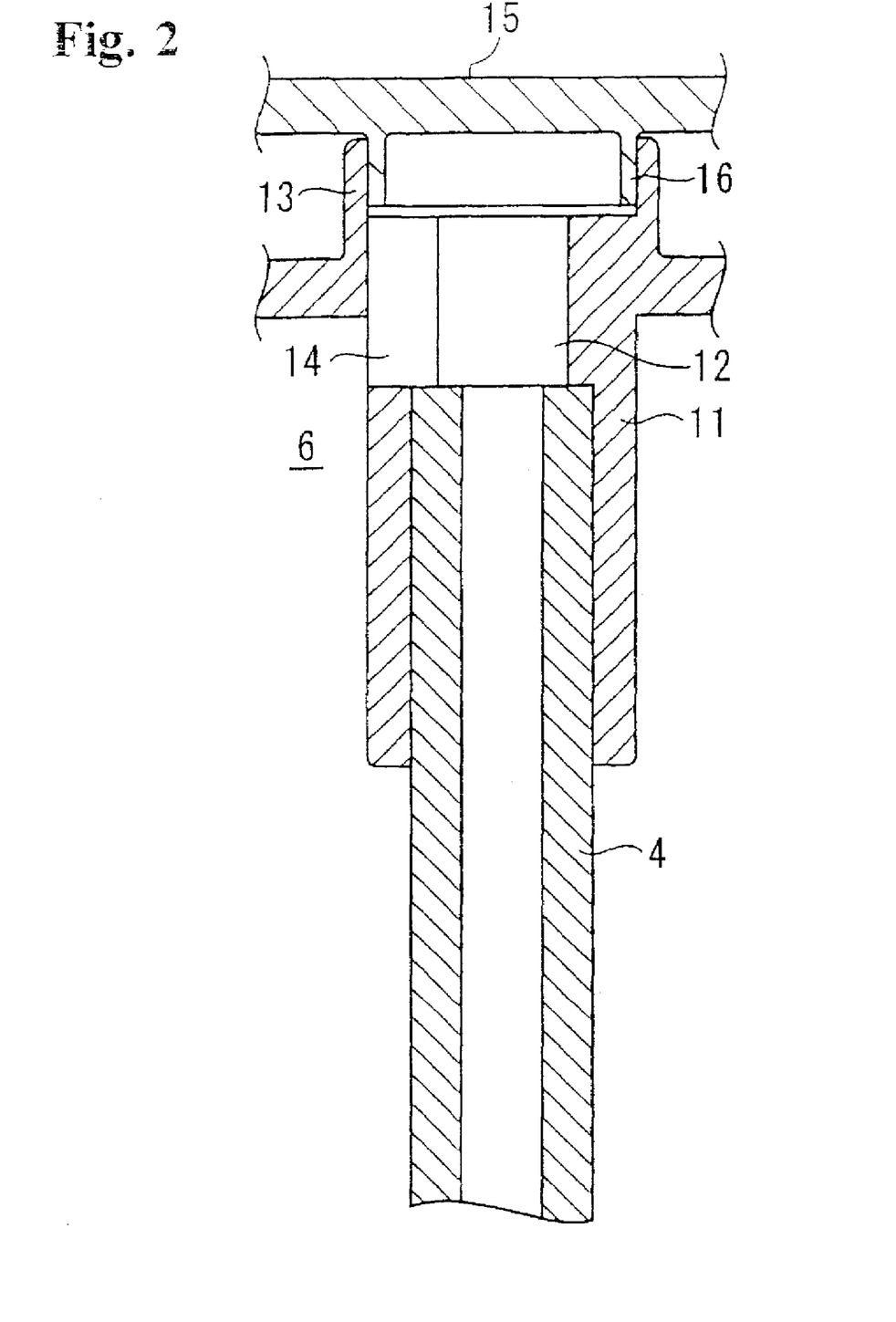
FIG. 2 is a side elevational view, partly in section, showing a central portion of a cap of the swab testing device of FIG. 1(a) and FIG. 1(b) when a top aperture of the cap is closed with a lid.
Figure 3:
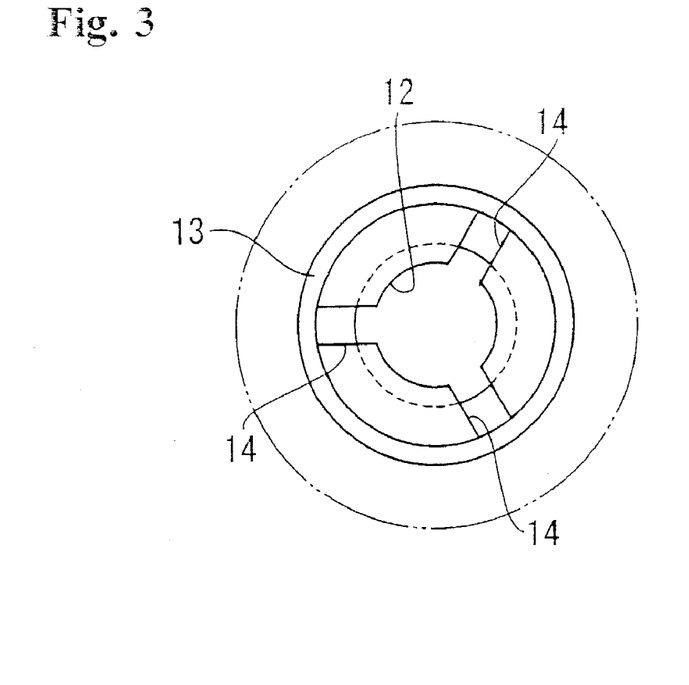
FIG. 3 is a top view showing the central portion of the lidded cap.

The construction of cap 10 will now be described in more detail in further reference to FIGS. 2 and 3. Cap 10 in this embodiment has a lid 15 that is detachably connected to the top of cap 10 to hermetically close an aperture 18 of cap 10 that communicates with hollow tube 11. As particularly shown in FIG. 5(a) to FIG. 5(c), lid 15 in this embodiment comprises an elongated flap having one end rotatably connected to a peripheral end of the top of cap 10, and a cylindrical boss 16 formed on and projected from the underside of the flap to be fittingly engageable with aperture 18. When boss 16 of lid 15 is engaged within an upstanding top portion 13 of hollow tube 11 that surrounds aperture 18, an interior or channel 12 of hollow tube 11 that communicates the interior of container 1 in a manner described hereinlater is hermetically closed and separated from the atmosphere.

A plurality of radial slits extends through the wall of hollow tube 11, which communicates with an interior 6 of container 1 beneath the underside of cap 10. Accordingly, when the top opening of container 1 is closed by cap 10, interior 6 of container 1 always communicates with inside channel 12 of hollow tube 11 but does not communicate with the atmosphere as far as boss 16 of lid 15 is fitted to hermetically close aperture 18 at the top of cap 10, which prevents leakage of diluent 7 or sample liquid in container 1 and also prevents contamination thereof caused by communication with the atmosphere. Once boss 16 of lid 15 is detached from top portion 13 of hollow tube 11 to open aperture 18, even if cap 10 still remains fitted onto container 1, inside channel of hollow tube 11 is open to the atmosphere to provide a passage allowing any liquid in container 1 to be discharged therefrom to the outside of container 1.

In the illustrated embodiment, there are three radial-extending slits 14 at equal spacing, that is 120-degree intervals, which is, however, only an example and may have another design as far as they function as bypass means for always connecting interior 6 of container and inside channel 12 of hollow tube 11 for liquid communication therebetween.

The swab testing device as above constructed is prepared such that a predetermined amount of diluent 7 is contained in container 1 that is hermetically sealed by cap 10 with lid 15 in a closed position, and then sterilized in an autoclave chamber or by radiation for storage and sale.

A swab testing method to be done by employing the above-described device will now be described. To start the swab testing, the device is held in an normal orientation as shown in FIGS. 1(a) and 1(b) and cap 10 is removed from container 1 to be drawn up in substantially an upright direction so that cotton swab 5 that has been long immersed in diluent 7 will be pulled up above the liquid level 8. When cotton swab 5 has been separated from the liquid level 8 and while it is still positioned within the intermediate container portion defined by surface 2 with scales 3, opposite surfaces 2, 2 are inwardly pressed by fingers to further reduce the distance between surfaces 2, 2. As described above, the distance between surfaces 2, 2 in a normal configuration of container 1 is determined to be slightly greater than the outer diameter of cotton swab 5, which is reduced to less than the outer diameter of cotton swab 5 by applying pressure with fingers while cotton swab 5 is passing through the intermediate portion of container 1 during the cap drawing operation, so that cotton swab 5 is squeezed to release an excessive amount of diluent 7 therefrom, which is again back to the container interior 1. It should be understood that the intermediate portion is easily collapsible and deformable under compression due to material characteristic of container 1 and an easy-grip design applied to the intermediate portion that depends on a pair of opposed, parallel surfaces 2, 2.

Though not illustrated, in another embodiment, the distance between surfaces 2, 2 of the intermediate reduced-diametric portion of container 1 made of hard plastic material is determined to be slightly smaller than the outer diameter of cotton swab 5. In this embodiment, cotton swab 5 will be automatically squeezed when passing through the intermediate portion of container 1 during the cap drawing operation, so that an excessive amount of diluent entrained in cotton swab 5 is separated therefrom to fall down toward a pool of diluent 7, with no need to manually apply internal pressure to surfaces 2, 2. The amount of diluent to be removed from cotton swab 5 will substantially depend on a difference between the distance between surfaces 2, 2 and the outer diameter of cotton swab 5.

As a result of manual or automatic squeezing of cotton swab 5 during the cap drawing operation, an excessive amount of diluent 7 separated from cotton swab 5 that now becomes to be ready for use in swabbing down a surface of a sample to be microbiologically inspected in a swab test. Since cotton swab 5 is secured to or integral with cap 10 into one unitary assembly, the swab test can easily be done by using cotton swab 5, while only the periphery of cap 10 is held by fingers, which do not affect the sterilized condition of cotton swab 5.

After cotton swab 5 is used to swab down the sample surface, it is then inserted into container 1 and container 1 is capped with cap 10. In the capped container 1, cotton swab 5 is again immersed in diluent 7. During insertion of cotton swab 5 into container 1, more specifically while cotton swab 5 passes through the intermediate reduced-diameter portion of container 1, some amount of a sample liquid, that comprise in main diluent 7 but may contain any microorganism that may exist on the sample surface, adhered to cotton swab 5 should be removed therefrom in the same manner with the cap drawing operation. More specifically, when the distance between surfaces 2, 2 in a normal configuration of container 1 is designed to be slightly greater than the outer diameter of cotton swab 5, by forcing surfaces 2, 2 to be deformed inwardly so that the distance therebetween is reduced to less than the outer diameter of cotton swab 5 during the cap inserting operation, cotton swab 5 is squeezed to release some amount of the sample liquid into a pool of diluent 7 in container 1. Alternatively, substantially the same function may automatically be given when cotton swab 5 passes through the reduced-diameter portion of container 1 during the cap inserting operation, where the distance between surfaces 2, 2 is originally designed to be slightly smaller than the outer diameter of cotton swab 5. Preferably, such squeezing operation is repeated several times so that a sufficient amount of the sample liquid is transferred from cotton swab 5 to the liquid pool in container 1. The capped container 1 is well shaked so that the sample liquid diluted with diluent 7 to have a predetermined dilution.

The diluted sample liquid is pipetted into a laboratory dish or tube to be cultured within a culture medium therein. The manner of pipetting will be described in reference to FIG. 4 and FIG. 5(a) to FIG. 5(c).

Figure 5A:
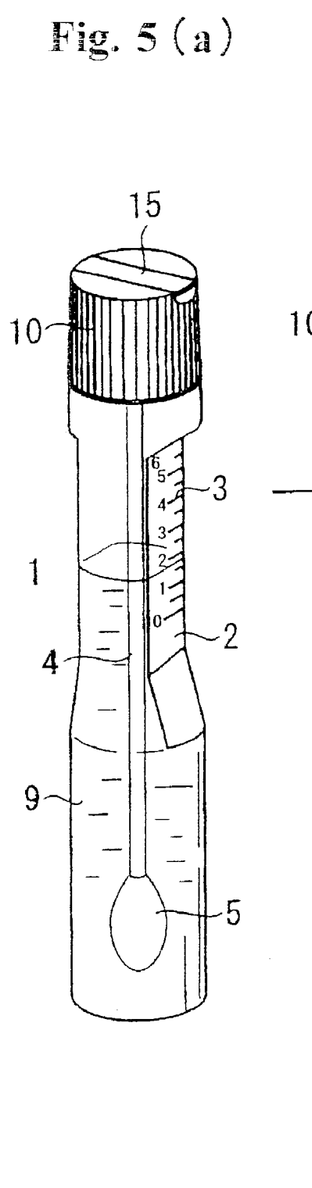
FIG. 5 is an explanatory view showing the pipetting operation to be done by utilizing this swab testing device.

FIG. 5(a) shows the swab testing device in a normal upstanding orientation, wherein the appropriately diluted sample liquid 9 is contained in interior 6 of container 1. As described before in reference to FIG. 2, though interior 6 of container 1 communicates with inside channel 12 of hollow tube 11 of cap 10 via bypass slits 14, sample liquid 9 in container 1 can never be discharged to the outside even if the swab testing device is reversed upside down, as far as boss 16 of lid 15 is engaged within top ring portion 13 of hollow tube 11 to hermetically seal aperture 18.

Figure 4:
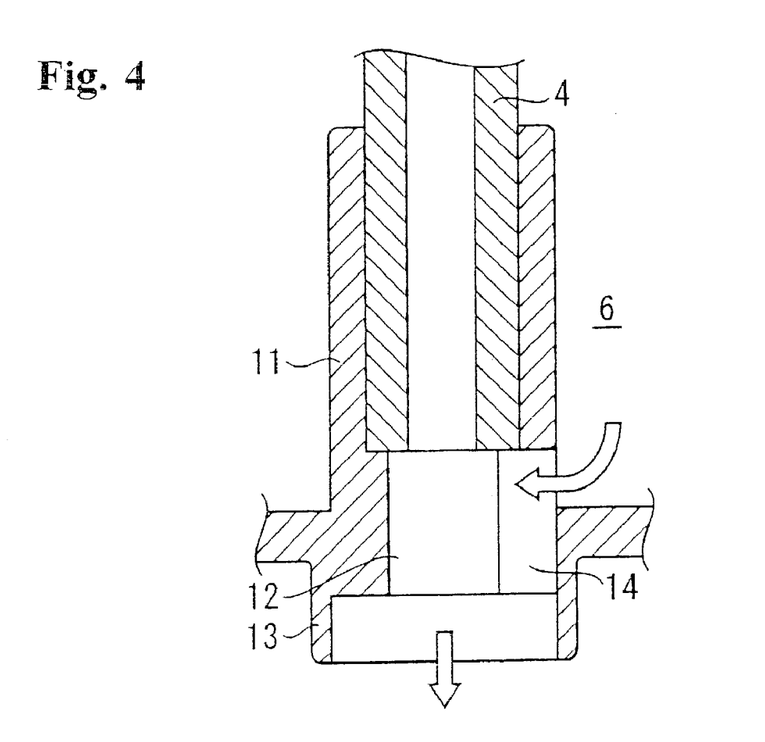
FIG. 4 is a side elevational view, partly in section, showing the central portion of the cap when the device is held upside-down and the lid is detached from the cap to allow discharge and pipetting of liquid therein.
Figure 5B:
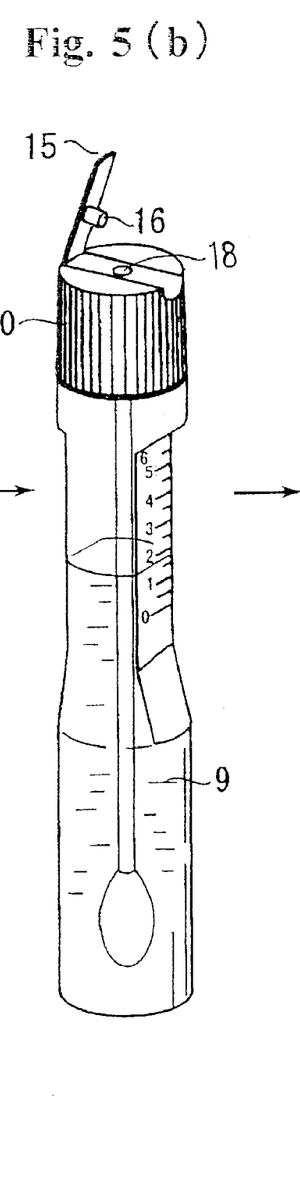
Figure 5C:
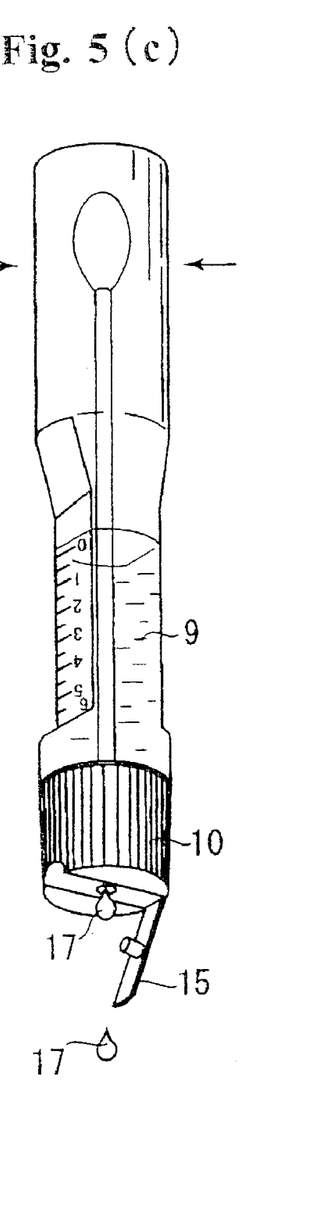

Then, lid 15 is opened, as shown in FIG. 5(b), and the swab testing device of FIG. 5(a) is held upside down, as shown in FIG. 5(b). Once lid 15 is opened, interior 6 of container 1 becomes communicatable with the outside or atmosphere via bypass slits 14 and inside channel 12, so that sample liquid 9 in container 1 is allowed to be gravitationally discharged through aperture 18, when the device is held upside down, as shown in FIG. 4. To enhance discharge of sample liquid 9 in container 1 to the outside through aperture 18, it is preferable that the lower portion of container 1 in upside-down orientation is compressed from opposite sides, as shown by arrows in FIG. 5(c), to pump up liquid sample 9 toward an exit, that is aperture 18. Liquid sample 9 is thus discharged through aperture 18 as droplets 17, because aperture 18 is very small in diameter.

In pipetting of sample liquid 9 from container 1 to any desired laboratory dish or tube, a predetermined amount of sample liquid 9 should be discharged through aperture 18 in careful reference to scales 3. More specifically, an amount of sample liquid 9 in container 1 is discharged and thrown away until the level 8 reaches the reference line identified by figure "0". At this time, container 1 contains a reference amount of sample liquid 9 and is now ready for starting pipetting. Then, while the device still remains to be held upside down, the lower portion of container 1 is compressed from opposite sides to pump up sample liquid 9 to be discharged from aperture 18 to a laboratory dish or tube. The liquid level 8 is gradually lowered as discharge of sample liquid 9 continues. When, for example, 3 ml of sample liquid 9 is to be pipetted, discharge of sample liquid 9 through aperture 18 is finished when the liquid level 8 reaches one of scales 3 that is identified by figure "3".

Figure 6:
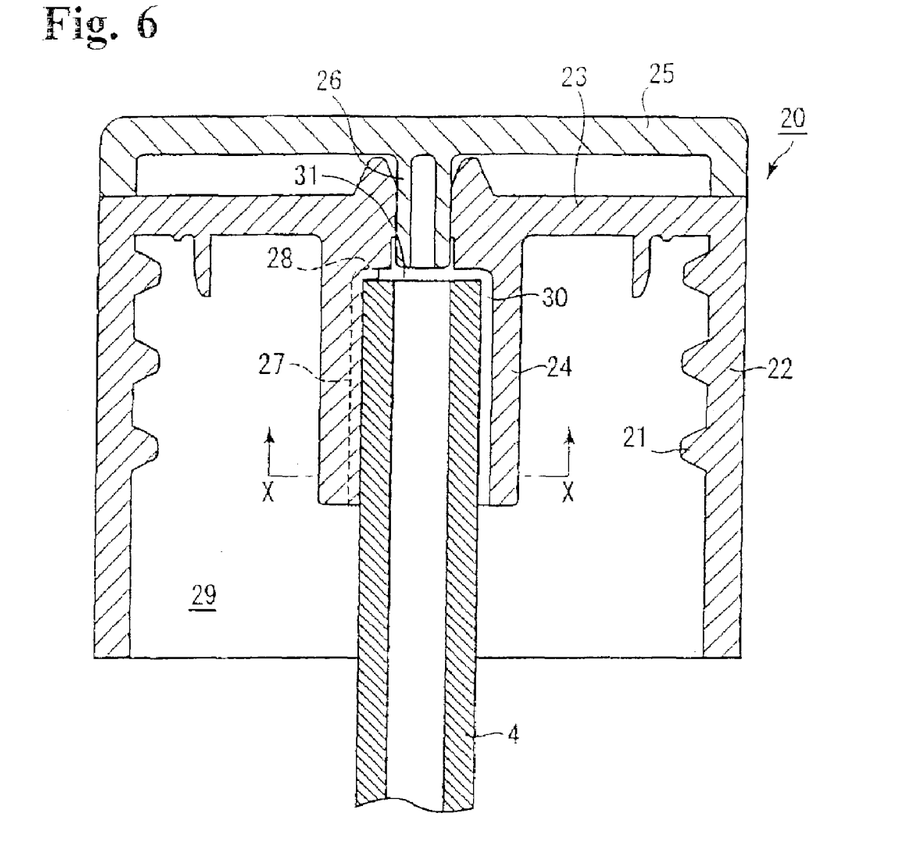
FIG. 6 is a cross-section showing a lidded cap and parts associated therewith of a swab testing device in accordance with another embodiment of the present invention.
Figure 7:
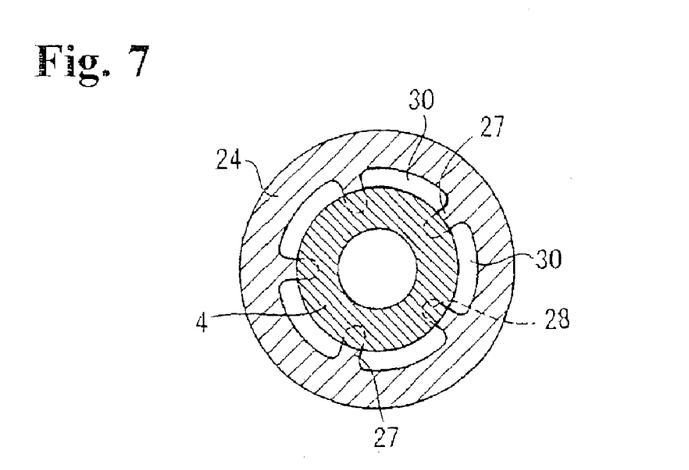
FIG. 7 is a cross-section taken along the lines X-X in FIG. 6.

FIGS. 6 and 7 illustrates another cap design of a swab testing device that also embodies the present invention. In this embodiment, a cap 20 comprises a side peripheral wall 22 with an internal thread 21 engageable with an external thread (not shown) on the mouth of container 1, a top wall 23 connected integrally to the upper end of side peripheral wall 22, a downward hollow tube 24 coaxial with side peripheral wall 22 and connected integrally to the center portion of the underside of top wall 23, and a lid 25 with a downward boss 26 hermetically engageable within an aperture 23a (FIG. 8) at a center of top wall 23.

The inner diameter of hollow tube 24 of cap 20 is designed to be slightly greater than the outer diameter of a stick 4. A plurality of spaced, axially extending projections 27 are formed on the inside surface of hollow tube 24 to cooperatingly surround and support stick 4. In this embodiment, five projections 27 extend axially with equal angular spacing between one another. The upper ends of projections 27 are directed inwardly to engage with the upper end of stick 4. Stick 4 is secured or bonded by any suitable means to hollow tube 24 in relative position with hollow tube 24 that has been just described above.

Figure 8:
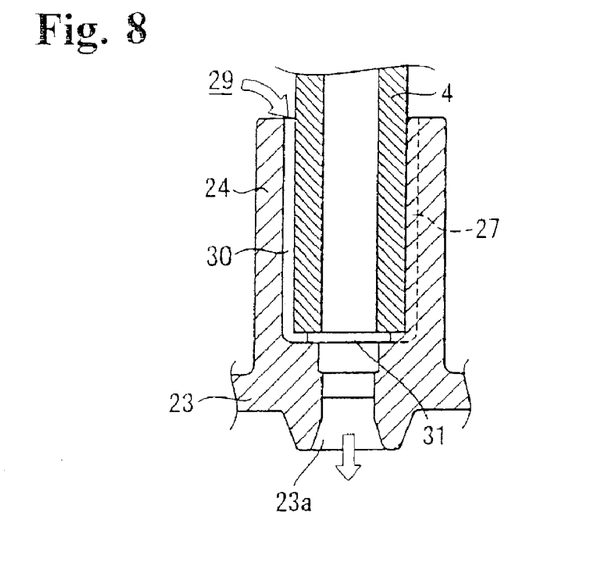
FIG. 8 is a side elevational view, partly in section, showing the central portion of the cap when the device is held upside-down and the lid is detached from the cap to allow discharge and pipetting of liquid therein.

With cap 20 as above constructed, each channel 30 is formed between adjacent two projections 27, 27. The lower end of each channel 30 communicates with an inside space 29 of cap 20 that will be a part of the interior of the capped container 1. The upper end of each channel 30 is communicatably connected to a gap 31 that is formed, due to the upper ends of projections 27 being directed inwardly to contact with the upper end of stick 4, between the upper end of stick 4 and the underside of top wall 23. Accordingly, the swab testing device with cap 20 in this embodiment will provide substantially the same function and utility with those of the first embodiment described in reference to FIGS. 1 to 5. When cap 20 is tightly mounted or screwed onto the mouth of container 1 so that the interior of container 1 is hermetically sealed, no leakage of any liquid in container 1 is possible, as far as central aperture 23a of top wall 23 is closed by boss 26 of lid 25. Once lid 25 is opened, however, the container interior becomes communicatable with the outside via channels 30, gap 31 and aperture 23a so that an amount of liquid in container 1 is allowed to be discharged through aperture 23a to the outside of the device by reversing the device upside down, as shown in FIG. 8, and depressing the bottom portion of container 1, as in a manner described in reference to FIG. 5(c). The arrows in FIG. 8 indicate flow of liquid to be discharged.

Although the present invention has been described and illustrated in conjunction with only several specific embodiments thereof, it should be understood that the present invention is not limited to these embodiments and involves various changes and modifications as far as they are deemed within the spirit and scope of the invention defined in the appended claims. For example, though stick 4 is shown as a hollow one in the illustrated embodiments, it may be a solid one.

A wall of a hollow stick 4 may be perforated to allow liquid communication between the inside and the outside of the stick 4. When, for example, hollow stick 4 of the embodiment shown in FIG. 6 is so designed, a predetermined amount of a diluent may be first poured into container 1 in such manner that a syringe needle is inserted into the upper end of stick 4, through aperture 23a of top wall 23 that has been opened by removing lid 25, so that the diluent injected from the syringe needle flows down through the inside of hollow stick 4 and is then dispersed toward the outside of hollow stick 4, that is the container interior, through perforations on the wall of hollow stick 4.

Figure 9:
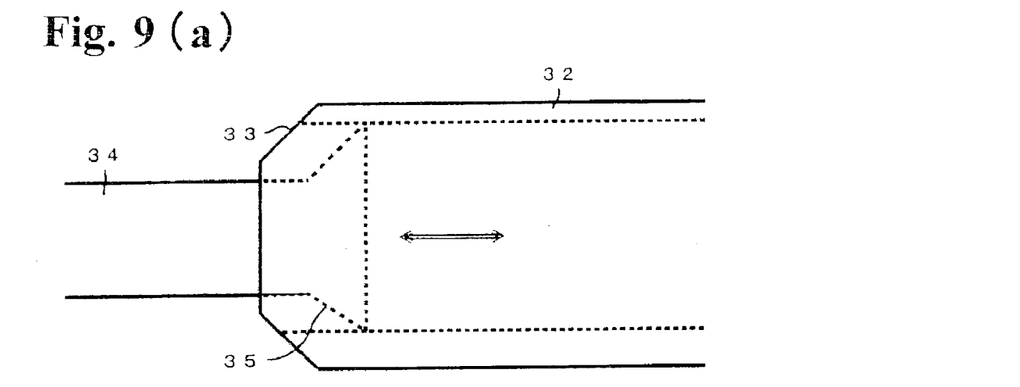
FIG. 9(a) and FIG. 9(b) show a telescopic stick that may be used in the swab testing device of the present invention.

Stick 4 may have a telescoping construction, examples of which are shown in FIG. 9(a) and FIG. 9(b). In the embodiment shown in FIG. 9 (a), a stick comprises a first member 32 that must be a hollow one and a second member 34, solid or hollow, telescoping within one end of first member 32. A cotton swab 5 is attached or connected to the other end (not shown) of first member or tube 32. Second member 34 is secured or connected to a cap (not shown) at one end thereof (not shown). A top opening end portion 33 is thermally processed, for example, to have a decreased diameter, while a corresponding end portion of second member 34 is enlarged to have a diameter much greater than the reduced diameter of the upper end of first member 32, thereby preventing removal or separation of second member 34 from first member 32, when second member 34 is pulled out of first member 32 to enlarge the axial length of the stick. The inner diameter of first member 32 is determined substantially the same with the outer diameter of an enlarged end portion or stopper 35 of second member 34 to allow stable fitting relation between first and second members 32, 34, as well as smooth sliding movement relative to each other.

A telescopic stick of another embodiment shown in FIG. 9(b) comprises a hollow, first member 32' having a cotton swab 5 at one end thereof (not shown) and a second member 34 that may be the same with that in the embodiment shown in FIG. 9(a). A portion in vicinity to the top opening of first member 32' is compressed by thermal press operation, for example, to provide a recess 33' for engagement with an enlarged end portion 35 of second member 34.

When a telescopic stick such as shown in FIG. 9(a) and FIG. 9(b) is used in the swab testing device of the present invention, its axial length may change from the minimum to the maximum, the minimum length being obtained when at least a part of second member 34 is received in first member 32, 32' and the maximum length being obtained when second member 34 is pulled out of first member 32, 32' until enlarged end portion 32 becomes engaged with stopper 33, 33'. The telescopic stick may be received in container 1 in its minimum length, which makes possible to reduce the lengthwise size of container 1. Nevertheless, the telescopic stick will automatically be extended to the maximum length by inwardly depressing opposite surfaces 2, 2 of the intermediate portion of container 1 to squeeze cotton swab 5 during the cap drawing operation. The maximum length of the stick 4 is good to be used in swabbing down the sample surface. When container 1 is to be again capped with a cap, the cotton swab 5 on the leading end of the stick 4 becomes contact with the bottom of container 1 during insertion of the stick 4 thereinto, so that the axial length of the stick 4 is reduced by its telescopic arrangement.

What is claimed is:

1. A swab testing device having a container containing a diluent, a cap detachably mounted on an opening of the container, an elongating stick secured to or integral with the cap, and a cotton swab connected to a leading end of the stick and immersed in the diluent when the container opening is closed with the cap, characterized in that:

(a) the underside of said cap includes a downward hollow tube having an inside diameter slightly greater than an outside diameter of said stick, and said hollow tube is provided with a plurality of inward projections cooperating with each other to surround and support said stick, thereby providing a plurality of communicating channels communicatable with an interior of said container and also communicatable with atmosphere by an aperture formed on said cap;

(b) said cap also includes a lid by which said aperture may be opened and closed; and (c) any liquid in said container may be discharged through said plurality of communicating channels and said aperture, when said lid is opened to communicate said plurality of communicating channels with atmosphere through said aperture, even when said container opening remains closed with said cap.

2. The swab testing device according to claim 1 wherein the underside of said cap includes a downward hollow tube with a plurality of slits extending therethrough, said hollow tube and said slits cooperate with each other to constitute said communicating channel.

3. The swab testing device according to claim 2 wherein said slits comprise a plurality of equally spaced, radially extending slits.

4. The swab testing device according to claim 1, wherein the upper ends of at least one of the inward projections inwardly extent toward a gap between the bottom of said hollow tube and the top of said stick, said spaces between adjacent inward projections and between said hollow tube and said stick and the gap between the bottom of said hollow tube and the top of said stick cooperate with each other to constitute said communicating channel.

5. The swab testing device according to claim 1 wherein the inward projections are integrally formed on the inside of said hollow tube with equal spacing.

6. The swab testing device according to claim 1 wherein said container is provided with a reference below a level of a liquid contained therein and plurality of scales still below said reference, when said container is held with said cap down, said reference indicating a liquid level from which pipetting should start and each of said scales indicating an amount of liquid that has been discharged or pipetted.

7. The swab testing device according to claim 1 wherein said container includes squeezing means for removing and recovering an excessive amount of liquid contained in said cotton swab when said cotton swab is drawn from said container during uncapping operating, as well as for removing and recovering sample liquid contained in said cotton swab when said cotton swab is inserted into said container during capping operation after said cotton swab has been used to swab down a surface of a subject to be bacteriologically or microbiologically inspected.

8. The swab testing device according to claim 1 wherein said stick is hollow, a hollow interior of said stick being a part of said communicating channel.

9. The swab testing device according to claim 1 wherein said stick is telescopic.

* * * * *